(12) United States Patent
Manke et al.

(10) Patent No.: US 9,737,280 B2
(45) Date of Patent: Aug. 22, 2017

(54) TUBE-DETECTOR ALIGNMENT USING LIGHT PROJECTIONS

(71) Applicant: KONINKLIJKE PHILIPS N.V., Eindhoven (NL)

(72) Inventors: Dirk Manke, Hamburg (DE); Christoph Kurze, Hamburg (DE); Richard Johannus Maria Van De Ven, Moergestel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 16 days.

(21) Appl. No.: 14/786,098

(22) PCT Filed: Apr. 16, 2014

(86) PCT No.: PCT/EP2014/057677
§ 371 (c)(1),
(2) Date: Oct. 21, 2015

(87) PCT Pub. No.: WO2014/173741
PCT Pub. Date: Oct. 30, 2014

(65) Prior Publication Data
US 2016/0074003 A1    Mar. 17, 2016

(30) Foreign Application Priority Data
Apr. 23, 2013   (EP) .................................... 13164897

(51) Int. Cl.
*A61B 6/08*    (2006.01)
*H01J 37/22*   (2006.01)
(Continued)

(52) U.S. Cl.
CPC ............ *A61B 6/587* (2013.01); *A61B 6/0492* (2013.01); *A61B 6/08* (2013.01); *A61B 6/4405* (2013.01);
(Continued)

(58) Field of Classification Search
CPC ........... A61B 6/00; A61B 6/04; A61B 6/0482; A61B 6/08; A61B 6/40; A61B 6/42;
(Continued)

(56) References Cited

U.S. PATENT DOCUMENTS 4,092,544 A    5/1978    Grim
4,836,671 A    6/1989    Bautista
(Continued)

FOREIGN PATENT DOCUMENTS

EP    2022403 A1     2/2009
WO    2011141763 A1  11/2011
WO    2013080111 A1   6/2013

OTHER PUBLICATIONS

Da Zhang et al, "A convenient alignment approach for x-ray imaging experiments based on laser positioning devices", Med. Phys. vol. 35 No. 11, Nov. 2008, pp. 4907-4910.

*Primary Examiner* — Anastasia Midkiff (57) ABSTRACT

The present invention relates to acquisition of medical image information of an object. In order to provide a user-friendly alignment of X-ray tube and a detector, optionally combined with an anti-scatter grid, an alignment arrangement is proposed, which comprises a tube attachment with a first light projection device and a detector attachment with a second light projection device. The first and second light projection devices each generate a light pattern on a projection surface. The tube attachment and the detector attachment can be brought into a correct spatial arrangement relative to each other by bringing the first light pattern in a predetermined spatial relation with the second light pattern on the projection surface.

13 Claims, 4 Drawing Sheets

(51) Int. Cl.
*G02B 27/64* (2006.01)
*A61B 6/00* (2006.01)
*A61B 6/04* (2006.01)
*A61N 5/10* (2006.01)
*H04B 10/00* (2013.01)
*G02B 7/00* (2006.01)

(52) U.S. Cl.
CPC .............. *A61B 6/585* (2013.01); *A61B 6/461* (2013.01); *A61B 6/547* (2013.01); *A61N 5/1048* (2013.01); *A61N 2005/105* (2013.01); *G02B 7/005* (2013.01); *G02B 27/64* (2013.01); *H01J 37/22* (2013.01); *H01J 2237/1501* (2013.01); *H01J 2237/20292* (2013.01); *H01J 2237/2482* (2013.01); *H01J 2237/24528* (2013.01); *H04B 10/22* (2013.01)

(58) Field of Classification Search
CPC ....... A61B 6/44; A61B 6/4405; A61B 6/4411; A61B 6/4429; A61B 6/4452; A61B 6/4454; A61B 6/4475; A61B 6/46; A61B 6/461; A61B 6/465; A61B 6/467; A61B 6/547; A61B 6/585; A61B 6/587; H05G 1/00; H05G 1/02; H05G 1/08; G01N 23/00; G01N 23/02; G01N 23/04; G01N 23/06; G01N 23/08; G01N 23/083; G02B 7/00; G02B 7/003; G02B 7/005; G02B 13/00; G02B 13/16; G02B 23/00; G02B 27/00; G02B 27/40; G02B 27/64; H04B 10/114; H04B 10/1141; H04B 10/116; H04B 10/22; H04B 10/50; H04B 10/501; H04B 10/502; H04B 10/503; H04B 10/516; H04B 10/548; H04B 10/556; H04B 10/5563; H04B 10/60; H04B 10/66; H04B 15/00; G01T 1/29; G01T 1/2907; G01T 1/2914; G01T 7/01; G01T 7/005; A61N 5/00; A61N 5/01; A61N 5/1048; A61N 5/1049; A61N 5/1064; A61N 5/1065; A61N 5/1067; A61N 2005/0626; A61N 2005/0632; A61N 2005/0664; A61N 2005/105; A61N 2005/1051

See application file for complete search history.

(56) References Cited

U.S. PATENT DOCUMENTS

| | | | |
|---|---|---|---|
| 5,241,578 A | 8/1993 | MacMahon | |
| 5,283,808 A * | 2/1994 | Cramer | A61B 6/08 378/205 |
| 5,388,143 A * | 2/1995 | MacMahon | A61B 6/08 378/154 |
| 6,447,164 B1 | 9/2002 | Polkus | |
| 7,736,055 B2 | 6/2010 | Hornig | |
| 2009/0190722 A1 * | 7/2009 | Windt | A61B 6/08 378/206 |
| 2011/0249793 A1 | 10/2011 | Lalena et al. | |
| 2012/0039447 A1 | 2/2012 | Lalena | |

* cited by examiner

TUBE-DETECTOR ALIGNMENT USING LIGHT PROJECTIONS

CROSS-REFERENCE TO PRIOR APPLICATIONS

This application is the U.S. National Phase application under 35 U.S.C. §371 of International Application No. PCT/EP2014/057677, filed on Apr. 16, 2014, which claims the benefit of European Patent Application No. 13164897.4, filed on Apr. 23, 2013. These applications are hereby incorporated by reference herein.

FIELD OF THE INVENTION

The present invention relates to medical image information acquisition of an object. In particular, the present invention relates to an alignment of an X-ray tube and an X-ray detector, in particular for mobile X-ray imaging applications. The invention further relates to a method for aligning an X-ray tube relative to a detector.

BACKGROUND OF THE INVENTION

In clinical practice, mobile X-ray imaging systems are used in cases, where patients are unable to leave the patient's bed and where it may become necessary to conduct medical imaging diagnostics in bedside situations. Such mobile X-ray imaging units can comprise a movable X-ray base unit, which may further be equipped with further functions and applications, such as image processing or control functions. For example, a movable base unit can further comprise a support arm, where an X-ray tube is mounted to.

A separate detector or detector panel receives the radiation, which has irradiated, for instance, a region of interest of a patient. The detector converts the detected radiation to electrical signals and can provide this image information to the base unit and the processing unit, for instance, via wireless or wired data connection. For the acquisition of an X-ray image, it can be important to adjust and align the X-ray tube and the detector at an optimal distance, a right angle, and correctly centered relative to each other. Especially, when additionally using an anti-scatter-grid, the grid and the tube have to be well aligned to avoid unwanted grid artefacts. Different technical approaches have been proposed to achieve a proper alignment of X-ray source and detector. U.S. Pat. No. 7,736,055 B2 describes an optical detection of deviations from an optimal arrangement using light reflectors at the detector, which reflect light transmitted by a light source arranged near the X-ray source. However, the practical usability of such arrangement solutions in clinical practice can often be very limited.

WO 2013/080111 A1, only relevant for novelty, discloses an X-ray imaging system comprises an X-ray tube, a ceiling suspension for the X-ray tube, a detector trolley with an X-ray detector mounted thereon, an active sensor matrix, an optical indication unit and a control unit. The active sensor matrix is fixedly mounted on the ceiling suspension, the optical indication unit is fixedly mounted to the detector trolley and is adapted for emitting an optical indication onto the active sensor matrix. WO 2011/141763 A1 discloses an apparatus for obtaining an intraoral x-ray image from a patient with an x-ray source and an intraoral image detector comprising one or more detectable elements. One or more sensors are positionally coupled near the x-ray source and are energizable to sense the location of the one or more detectable elements when the intraoral image detector is within the patient's mouth.

SUMMARY OF THE INVENTION

Hence, there may be a need for a more user-friendly alignment solution to achieve a correct alignment of an X-ray tube and a detector in medical imaging applications.

The object of the present invention is solved by the subject-matter of the independent claims, wherein further embodiments are incorporated in the dependent claims.

It should be noted that the following described aspects of the invention also apply for the method for aligning an X-ray tube relative to a detector.

According to the invention, an alignment arrangement for X-ray imaging is provided, which comprises a tube attachment with a first light projection device, and a detector attachment with a second light projection device. The tube attachment is configured to mount the first light projection device to an X-ray tube. The detector attachment is configured to connect the second light projection device to a detector. The first light projection device is adapted to generate a first light pattern on a projection surface and the second light projection device is adapted to generate a second light pattern on the projection surface. The first light pattern is in a predetermined spatial relation with the second light pattern on the projection surface in the event that the tube attachment and the detector attachment are correctly spatially arranged relative to each other.

For example, the first light pattern is in a predetermined spatial relation with the second light pattern on the projection surface in the event that the tube attachment and the detector attachment are in a correct spatial arrangement relative to each other. The correct spatial arrangement can be predetermined.

An advantage can be seen in a simple and intuitive way to achieve a desired adjustment of an X-ray tube and a detector. Furthermore, all three adjustment criteria (angular orientation, centering, and source image distance) can be represented commonly and reflected in one single alignment mechanism. This can lead to fewer artefacts due to better alignment, which can result in better image quality. Due to use of visible light pattern, navigation and adjustment can be more intuitive for medical staff and does not require extensive additional training.

The use of light sources, furthermore, allows use of mature and available technologies. Also no electromagnetic compatibility issues need to be addressed and no additional cumbersome mechanical devices are necessary, which may require difficult handling procedures.

The term "alignment" relates to a positioning of the X-ray tube and the detector in regards to distance, centering, and angle. An alignment can be achieved, for instance, by moving the X-ray tube, for example, by manual turning or shifting, or by displacing or moving the detector relative to its position relative to the X-ray tube.

"X-ray imaging" describes all imaging methods and applications, where used for generation of image information of a region of interest of an object.

For example, the alignment arrangement can be used in bedside X-ray imaging systems.

The term "tube attachment" relates to a possibility to mount the first light projection device to an X-ray tube. In other words, a movement of the tube directly correlates to a movement of the tube attachment. For example, the first light projection device can be mounted at the tube head. In addition to a direct mechanical mounting, also indirect coupling can be used. For example, a data connection can exchange position information and can control actuators or sensors to allow a remote coupling of the X-ray tube position and a position of the first light projection device.

The term "mounting" of the first light projection device to the X-ray tube can relate to different kinds of achieving a fixed correlation between the first light projection device and the X-ray tube. This includes any mechanical means, such as screws, welding, clamping, bonding, or others, but also an indirect linking via a data connection, which can control actuators to synchronize the spatial positions of the X-ray tube and the first light projection device.

Related to the detector attachment, the term "connect" can relate to a mechanical connection by integrating the light source or light projection device into an edge of the detector attachment.

The mentioned "spatial relation" can relate to a situation, where a spatial alignment between the X-ray tube and the detector occurs.

In one example, the predetermined spatial relation of the two light patterns only occurs in the event in which the X-ray tube and the detector are correctly aligned.

The term "correctly" can relate to an optimal arrangement of the X-ray tube and the detector relative to each other in terms of certain criteria, such as image quality, patient X-ray dose, detector size, image size and others.

A light projection device can be, for example, a lamp or laser source generating visible light. Furthermore, also light emitting diodes (LED) or similar technologies can be used. A laser light source can have advantages over a conventional light source, in particular related to brightness, preciseness, control, diffusion and other criteria.

A detector attachment can be, for instance, a rigid frame, where a detector is inserted, or any means, which allow a mounting of a light source to a detector.

For example, a detector or a detector panel, and the detector attachment are combined in a single part.

In another example, the detector and the detector attachment can be separate parts, which can allow a use of different detector panels or detector modules within the same detector attachment or detector frame, for example, for different imaging purposes.

A detector relates to any image receptor device, which is able to detect X-ray radiation and convert the detected radiation into electric signals, which can be processed further, for instance, by an image processor. Examples are digital flat panel detectors, CR cassettes or analog film cassettes. Digital detectors can comprise a scintillator layer and photodetector or pixel cells. In addition, an anti-scatter-grid can be mounted or disposed along with the detector. The grid can be, for instance, arranged in front of the detector in X-ray tube direction. In other words, the term "detector" can also relate to a combination of the detector itself combined with an anti-scatter grid.

The first light pattern can be, for instance, a projected line or a plurality of lines, generated with a laser light source. The light pattern can have a filled shape or an arrangement of different shapes or lines, which allow a representation of angular orientation, centering of X-ray tube and detector, and of the source image distance.

In one example, the projected light pattern is a set of multiple lines forming a rectangle or square.

The projection surface can be any light reflecting medium, where the light becomes visible to a user or to a sensing device.

In an example, this projection surface can be a bed sheet of a patient's bed, a surface of a patient support or a similar surface.

The second light projection device can be, for instance, a light source or a plurality of light sources, disposed in or at the detector attachment.

For example, a direction of a light projection can be sidewards parallel to a surface of the detector attachment or the detector. Such a sideward projection can have advantages, for instance, in the event that the detector attachment along with a detector is covered by the body of a patient and therefore invisible to the user. Light beams generating a sideward projection can thus visually indicate a position of the detector attachment or the detector itself, even if the detector or the detector attachment is not visible to the radiologist.

The "spatial relation of the first and second light pattern on the projection surface" relates to any pre-defined position of the two light patterns relative to each other.

For example, lines projected from the first and second light projection device can superpose, in order to allow an intuitive alignment process to the user.

In an example, the "predetermined spatial relation of the first light pattern with the second light pattern" can relate to an aligned situation.

According to one example, the first and/or second light pattern on the projection surface comprises a plurality of lines.

An advantage can be seen in the possibility for a user to exactly align the two light patterns in a certain dimension.

For example, an angular alignment or correct angular orientation can be achieved by bringing a projected line from the first projection device in superposition with a line projected by the second light projection device.

In another example, a correct source image distance can be adapted by bringing the individual length of two projected lines into alignment such that both line lengths are equal.

According to an example, the light pattern of the second light projection device indicates a spatial position of edges of the detector attachment.

An advantage can be seen in a workflow improvement, because the detector position can be indicated or determined, even if the detector is not visible to the user, for instance, covered by the patient.

According to an example, the second light projection device of the detector attachment generates fan shaped light approximately perpendicular to the projection surface.

An advantage of a fan shaped beam approximately perpendicular to the projection surface can be, that a projection surface can be located in a deviating height from the light source or a deviating height of the detector attachment. This means that even if the position of the detector attachment changes relative to the projection surface, the light pattern is still visible to the user.

According to an example, the first and/or second light projection devices are configured to adapt the light pattern to a plurality of predetermined spatial arrangements of the tube attachment and the detector attachment.

In other words, the light pattern can have different sizes and shapes depending on the desired position of the X-ray tube and the detector relative to each other.

An advantage can be seen in a possibility for the tube attachment and the detector attachment to adapt different spatial arrangements.

According to an example, the detector attachment is a detector receiving device configured to support and/or accommodate a detector.

An advantage can be that an exchange of detectors or a replacement of detectors is possible while maintaining the adjustment arrangement. Reason is that detector technologies can change over time due to technological development or due to the fact that different detectors may be used for different imaging purposes. A detector receiving device can allow a replacement of the detector itself while the detector attachment or the detector receiving device can be reused. This way, for example, a cost for upgrading such medical imaging systems can be lowered.

According to the invention, a medical X-ray imaging system is provided that comprises an X-ray tube, a detector, and an alignment arrangement according to any of the above mentioned examples. The X-ray tube and the detector are adapted to acquire an image of a region of interest of an object, A spatial arrangement of the X-ray tube and the X-ray detector relative to each other is adjustable, wherein the tube attachment is mounted to the X-ray tube and the detector attachment is mounted to the detector such that the X-ray tube and the detector are in a correct spatial arrangement relative to each other when the first light pattern is in the predetermined spatial relation with the second light pattern on the projection surface.

According to the invention, also a method for aligning an X-ray tube relative to a detector is provided. The method comprises the steps of:

providing an X-ray tube and an X-ray detector;

generating a first light pattern with a first light projection device, wherein the first light projection device is adapted to generate a first visible light pattern on a projection surface;

generating a second light pattern with a second light projection device, wherein the second light projection device is adapted to generate a second visible light pattern on the projection surface, and wherein the first light pattern on the projection surface is in a determined spatial alignment with the second light pattern on the projection surface in the event that the X-ray tube and the detector are correctly spatially arranged relative to each other; and adjusting a spatial position of the X-ray tube and the detector relative to each other such that the first light pattern is in the determined spatial alignment with the second light pattern.

It can be seen as an idea of the invention, to simplify the process of the alignment of an X-ray tube and a detector during a mobile X-ray imaging application by using intuitive light patterns which can be brought into alignment by medical staff, in order to achieve a correct arrangement of an X-ray tube and a detector relative to each other.

In other words, more generally, as a user with his human senses in many cases cannot exactly assess, whether two objects are correctly positioned in a three-dimensional room in relation to each other, an auxiliary arrangement is facilitated to represent the position information of a spatial arrangement in a common projection of two light patterns, where each light pattern represents one object. This allows an adequate visual representation of characteristics of a given arrangement of an X-ray source and a detector to the user.

BRIEF DESCRIPTION OF THE DRAWINGS

Exemplary embodiments of the invention will be described in the following with reference to the following drawings.

DETAILED DESCRIPTION OF EMBODIMENTS

Figure 1:
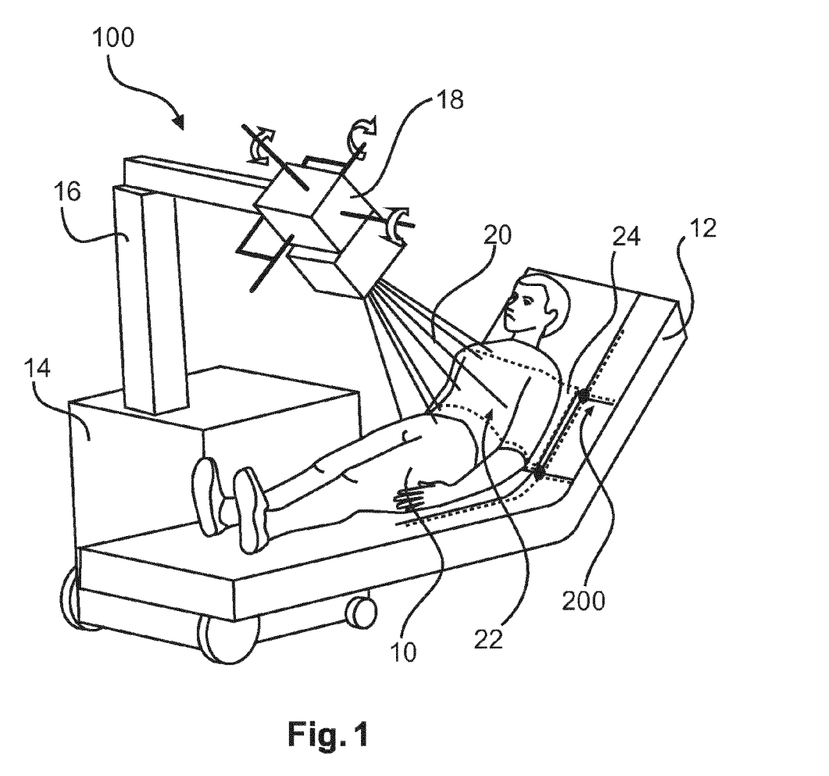
FIG. 1 schematically illustrates an example of a medical X-ray imaging at a patient's bed.

In FIG. 1, a medical X-ray imaging system 100 is shown in a bedside medical imaging situation. In the shown example, medical image information is acquired of an object 10 positioned on a patient support 12, wherein the patient support 12 also serves as projection surface. The imaging system 100 comprises a movable base unit 14, a support arm 16, and a spatially adjustable X-ray tube 18. The X-ray tube 18 generates and emits X-ray 20 towards the object 10 and irradiates a region of interest 22. A detector 24 is positioned between the patient support and the region of interest 22. The detector 24 can be, for example, a portable detector panel, which can have a cable or wireless data connection and/or a power supply connection with the base unit 14. In preparation for a medical imaging, the portable detector is manually positioned behind the region of interest 22. For this purpose, it may become necessary for the patient to raise or lift parts of his body, for instance, the upper part of the body, to allow inserting of the detector 24.

In an example, an anti-scatter-grid is additionally inserted between the region of interest 22 and the detector 24, wherein the detector 24 and the anti-scatter-grid (not shown) are mounted to each other. The existence of an anti-scatter grid can be seen as one reason for the required alignment precision.

In order to achieve a satisfying image quality, the X-ray tube 18 and the detector 24 need to be correctly aligned in terms of angular orientation, centering, and the correct source image distance. Therefore, it may become necessary for the radiologist to adjust a position of the X-ray tube 18 such that it comes into a defined arrangement with the detector 24. This can be achieved, for instance, by manual shifting and/or turning the X-ray tube, but also by shifting and turning the detector 24 or also both detector 24 and X-ray tube 18. Instead of moving the detector 24 separately, also the entire arrangement of the patient support, the detector 24, and the object 10 can be moved. This can be done, for example, by displacing the patient's bed within a patient's room.

In order to support and simplify the alignment between the X-ray tube 18 and the detector 24, an alignment arrangement 200 is facilitated to simplify the alignment process.

Figure 2:
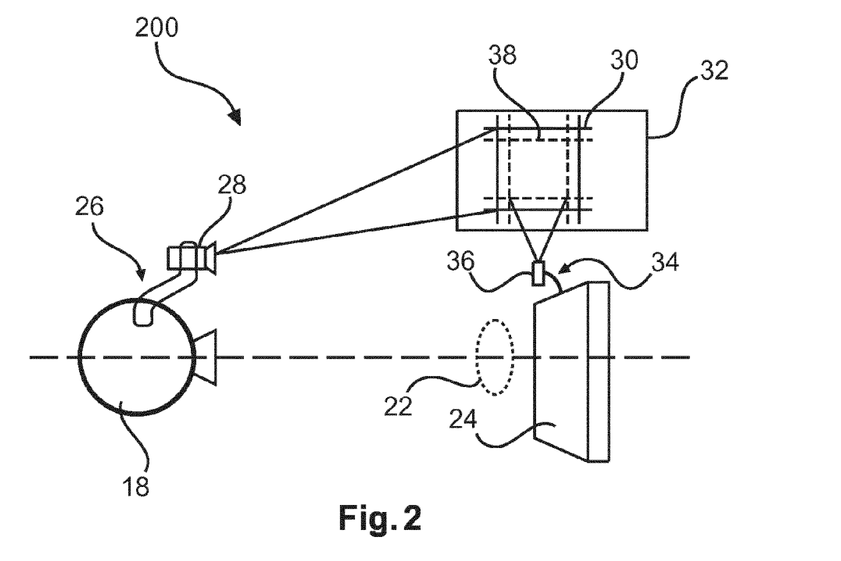
FIG. 2 shows a schematic overview of an alignment arrangement for X-ray imaging; m FIGS. 3A to 3H schematically illustrate an alignment situation and different misalignment situations.

In FIG. 2, an example of such an alignment arrangement 200 is described in more detail.

An X-ray tube 18 and a detector 24 are in one example arranged and configured to acquire image information of a region of interest 22 of an object 10. These components are not part of the alignment arrangement 200 and only shown for a better understanding of the overall system.

The alignment arrangement 200 comprises a tube attachment 26 with a first light projection device 28. The tube attachment 26 is adapted to mount the first light projection device 28 to the X-ray tube 18. The first light projection device 28 generates a first light pattern on a projection surface 32. A detector attachment 34 connects a second light projection device 36 to the detector 24. The second light projection device 36 is adapted to generate a second light pattern 38 on the same projection surface 32. The projection surface 32 can be, for instance, a bed sheet of a patient's bed and/or parts of the patient's body surface. Both, the first light pattern 30 and the second light pattern 38 are visible, for instance, as a combined line pattern on the common projection surface 32.

In one example, only parts of the first and/or second light pattern are visible. The number of light sources of the light projection devices 36 can be big enough to provide a certain redundancy in terms of information of the indicated position of the detector 24 or the detector attachment 34. This can mean, in the event, that some of the entirety of light sources of the light projection device 36 are covered (e.g. by a patient) and therefore invisible, an alignment can still be possible with the remaining light sources.

In further examples, the second light projection device 36 can comprise a higher number of light sources, for instance, 8, 10, 12, 20 or 50.

The first light pattern 30 and the second light pattern 38 can be brought into a predetermined spatial relation relative to each other on the projection surface 32. In the event of such predetermined spatial relation or alignment, the corresponding tube attachment 26 and the detector attachment 34 are also in a correct spatial arrangement relative to each other. In other words, the X-ray tube 18 and the detector 24 are correctly spatially arranged relative to each other, in the event, that the first light pattern 30 and the second light pattern 38 are aligned relative to each other on the projection surface 32.

For example, the correct spatial arrangement is predetermined, e.g. a predetermined spatial alignment.

It may be necessary in a preparation or configuration step to define and adjust both the X-ray tube 18/detector 24 arrangement and the corresponding predetermined spatial relation of the first light pattern 30 and the second light pattern 38 such that in case of an alignment of the first light pattern 30 with the second light pattern 38, the correct spatial arrangement, i.e. the correct spatial alignment of the X-ray tube 18 and the detector 24 is achieved.

A correct alignment is related to a spatial position and orientation of the X-ray tube 18 and the detector 24, respectively an optional anti-scatter grid, within certain tolerable deviations. In case of such combined detector/grid arrangement, such tolerable alignment errors can be, for instance, (if occurring individually) an orientation error of less than 3 degrees, a de-centering error less than approximately 7 cm, and a source image distance error less than approximately 40 cm. It is known, that the source image distance (SID) has a strong influence on the applied radiation dose. Therefore, in clinical practice of mobile radiography, a correct alignment of the X-ray tube and the detector can play an important role.

The light projection devices 28, 36 can be configured to generate different shapes of light patterns. For instance, a fan shaped light beam, generated by the second light projection device 36 and oriented perpendicular to the projection surface 32, can be used to generate a line pattern on the projection surface 32.

The detector 24 can be supplemented with an anti-scatter-grid (not shown), which has a defined orientation. It can be necessary to align the grid with the X-ray source and detector to minimize artefacts and improve image quality. The anti-scatter-grid filters scattered radiation by means of a, for instance, lamella grid and is mounted, for instance, clicked or clamped, onto the detector or mounted in any other way to the detector or detector attachment 34.

The projection surface 32 can be, for example, a side extension of the detector or the detector attachment, which surface at least partially reflects the light.

In another example, the projection surface can also be a surface of the patient itself or of an object 10 or a region of interest 22. In another example, the projection surface can also be dust particles in the air reflecting visible light to make a light beam itself visible.

The projection surface must not necessarily be parallel to the detector or to the detector attachment, however, the spatial relation between the X-ray tube 18, the detector 24 and the projection surface 32 is known and defined and is considered in the geometric model of the alignment arrangement.

The second light projection device 36 can be adapted to generate different shapes of light or patterns, for instance cone shaped, fan shaped, linear and others. For example, a direction of projection can be sidewards parallel to a surface of the detector or detector attachment. Thereby, as an example, light emitting diodes (LED) or small laser light sources can be used. An advantage can be that such light emitting diodes or laser light sources can be sourced inexpensively in many different variations. The second light projection device 36 can also be a plurality of separate light sources which are arranged at different locations, for instance, around the edges and corners of a detector attachment 34 to allow an indication of where edges or corners of the detector or the detector attachment are located. A spatial orientation and characteristics of the fan shape of the light beam, generated by the second light projection device, should be taken into consideration, in order to consider possible position deviations of the detector 24 or detector attachment 34, such as a different distance from the projection surface 32 due to, for instance, flexibility of the mattress surface.

In FIG. 3A to FIG. 3H, examples of an aligned and several misaligned situations are illustrated in a top view onto a detector surface, for instance, from an X-ray tube perspective. A detector attachment 34 is shown, for instance with an inserted detector 24 (not shown), where an attached second light projection device 36 (not shown) generates a second light pattern 38 on a projection surface (not shown). The light pattern 38 in this example comprises six separate projected lines, which indicate corners or edges of the detector attachment 34. The second light pattern 38, therefore, moves accordingly, when the detector attachment 34 changes its position. In other words, the six shown line projections indicate a position of the detector attachment 34 and the detector 24.

In addition to the second light pattern 38, a first light pattern 30 is projected onto the same projection surface 32 and the detector attachment 34. The first light pattern 30 is generated, for instance, by a first light projection device 28 (not shown), which can be mounted to a head of the X-ray tube 18 (not shown). Both the first light pattern 30 and the second light pattern 38 are lines, which allow an alignment in terms of angular orientation, centering, and source image distance.

Figure 3A:
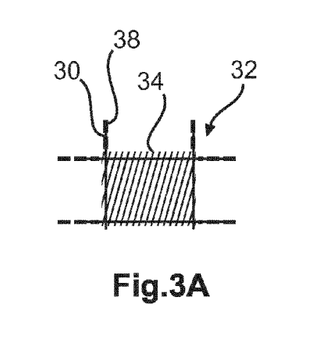

In FIG. 3A, a fully aligned situation is shown. This means that the first light pattern 30 and the second light pattern 38 superpose. In other words, in this case an alignment is achieved and the X-ray tube 18 and the detector 24 are correctly positioned relative to each other.

Figure 3B:
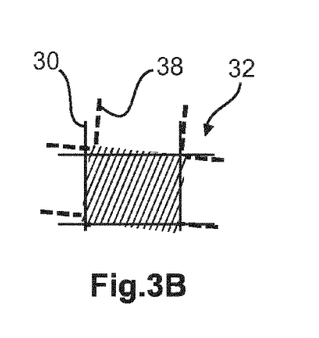

In FIG. 3B, a situation is shown, where the first light pattern 30 and the second light pattern 38 comprise a rotational error relative to each other. This means, that the X-ray tube 18 has an angular position orientation error relative to the detector 24.

Figure 3C:
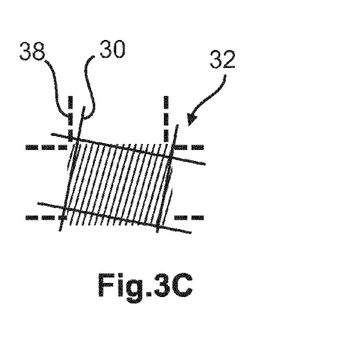

FIG. 3B and FIG. 3C show such an angular orientation error in respectively different rotational directions.

Figure 3D:
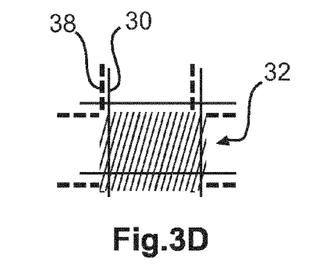

In FIG. 3D, the two light patterns 30, 38 are shifted relative to each other, which means that the X-ray tube 18 is shifted relative to the detector 24.

Figure 3E:
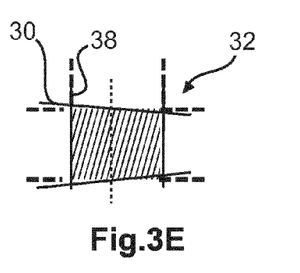

In FIG. 3E, the tube is tilted around a vertical axis, which results in a first light pattern 30, wherein the upper and lower line are not extending parallel.

Figure 3F:
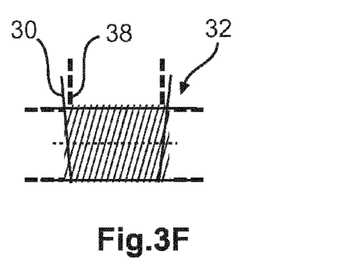

In FIG. 3F, an analog situation is illustrated, where the X-ray tube 18 is tilted around a horizontal axis relative to the detector 24. This results in a non-parallel extending of the vertical lines of the first light pattern 30.

Figure 3G:
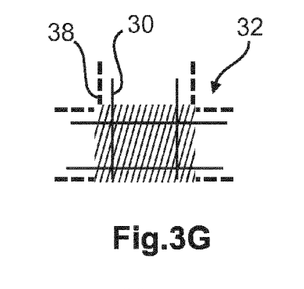
Figure 3H:
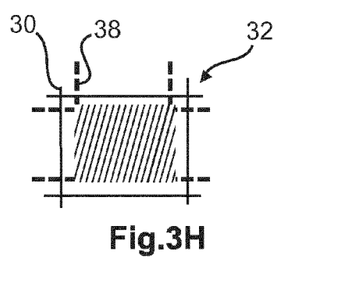

The source image distance is of particular relevance to image quality. As the size and shape of the first light pattern 30 corresponds to a predetermined or preset source image distance, a change of the source image distance therefore results in a change of the dimension or size of the first light pattern 30. In other words, at the correct source image distance, the projected first light pattern 30 has a predetermined extension or dimension. For example, such a size of the first light pattern 30 can match the size or position of the second light pattern 38 to allow an intuitive alignment of the two patterns 30, 38.

For example, in FIG. 3G, the source image distance is too small, whereas in FIG. 3H, the source image distance is too large.

In other words, FIG. 3A to FIG. 3H illustrate examples of different types of tube detector misalignments and can provide an indication, which correction needs to be performed, in order to correctly align the two light patterns 30, 38 and consequently the alignment of X-ray tube 18 and the detector 24.

Figure 4A:
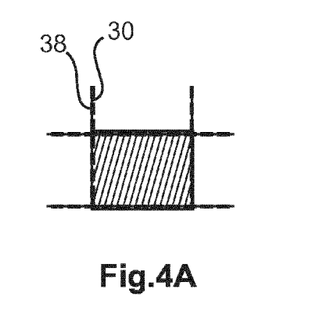
FIGS. 4A to 4C illustrate different options for light patterns on a projection surface.
Figure 4B:
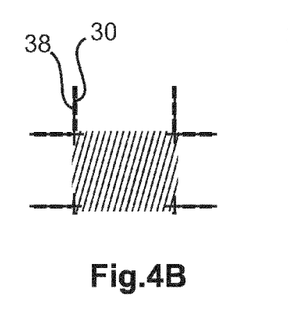
Figure 4C:
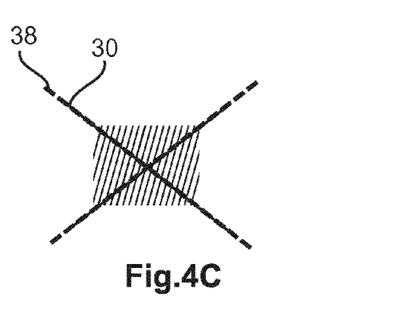

In FIG. 4A to FIG. 4C, examples of different light projection patterns for tube-detector alignment are shown.

Generally, there are many different possibilities of projection shapes and forms, such as single lines, a plurality of lines, parallel lines, angularly arranged lines, double lines, triple lines, circles, but also dotted lines and others. The pattern can, for example, be also a group of multiple lines in a certain angular alignment to each other, for instance for orthogonally arranged pairs of lines indicating a target position of a detector.

In an example, the first and second light pattern 30, 38 can have different light colors. An advantage can be that a user can easily distinguish between the first light pattern 30 and the second light pattern 38.

In another example, different light colors are used within the same detector attachment 34. In other words, different corners of a detector attachment 34 generate a red, a blue, and a green light pattern indicating a correct position and angular orientation of the detector 24 and the detector attachment 34.

In an example, in case of the predetermined spatial alignment of the first and second light pattern 30, 38, both patterns at least partially superpose on the projection surface 32. An advantage can be that an exact alignment can be achieved by superposing two similar projection shapes.

Figure 5:
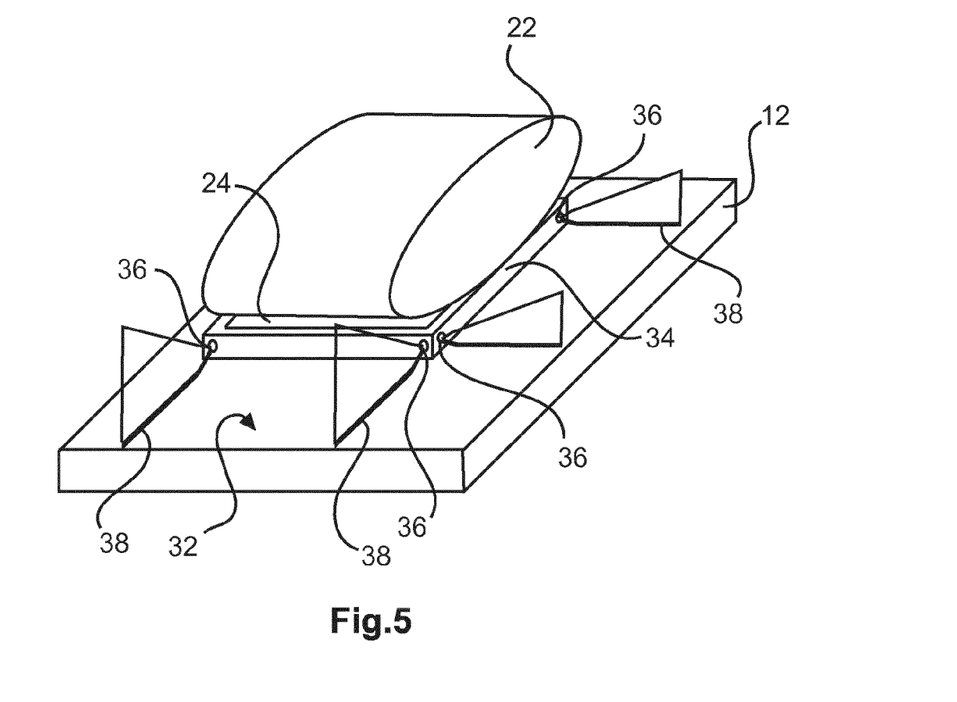
FIG. 5 schematically shows a patient body/detector arrangement in a bedside situation.

In FIG. 5, a region of interest 22 is shown, which is positioned on a patient support 12. The patient support 12 can be, for instance, a mattress of a patient's bed. Between the region of interest 22 and the patient support 12, a detector attachment 34, in which a detector 24 is inserted, is positioned. The detector attachment 34 comprises several second light projection devices 36, which are arranged at the corner areas of the edges of the detector attachment 34. The multiple second light projection devices 36 generate fan shaped light and thus generate multiple second light pattern 38, which are line shaped. The projection surface 32 is at least partly the support surface of the object 10 and the region of interest 22.

An advantage of a use of a support surface, for instance a mattress or bed sheet, can be that the detector 24 itself can be kept compact in its size, in particular when it's a wireless and/or mobile detector. The second light pattern 38 can be completely projected onto a bed surface or can also include other parts, such as an extension of the detector attachment 34.

In the shown example, the second light pattern 38 of the multiple second light projection devices 36 indicates a spatial position of the edges of the detector. An advantage is that in case of a complete covering of the detector or the detector attachment by a patient, a position can be indicated to a user by visually extending the edges. Such an indication of the positions of the edges can be achieved by an arrangement of the light projection devices 36 near corners of the detector attachment 34 or at the position, which correlates to a position of edges of the detector within the detector attachment 34. Each light projection device 36 can generate a fan shaped light beam, which fan is arranged perpendicular to the projection surface 32. The direction of the fan is such that the edge is visually elongated beyond the outer limits of the detector attachment 34.

Figure 6:
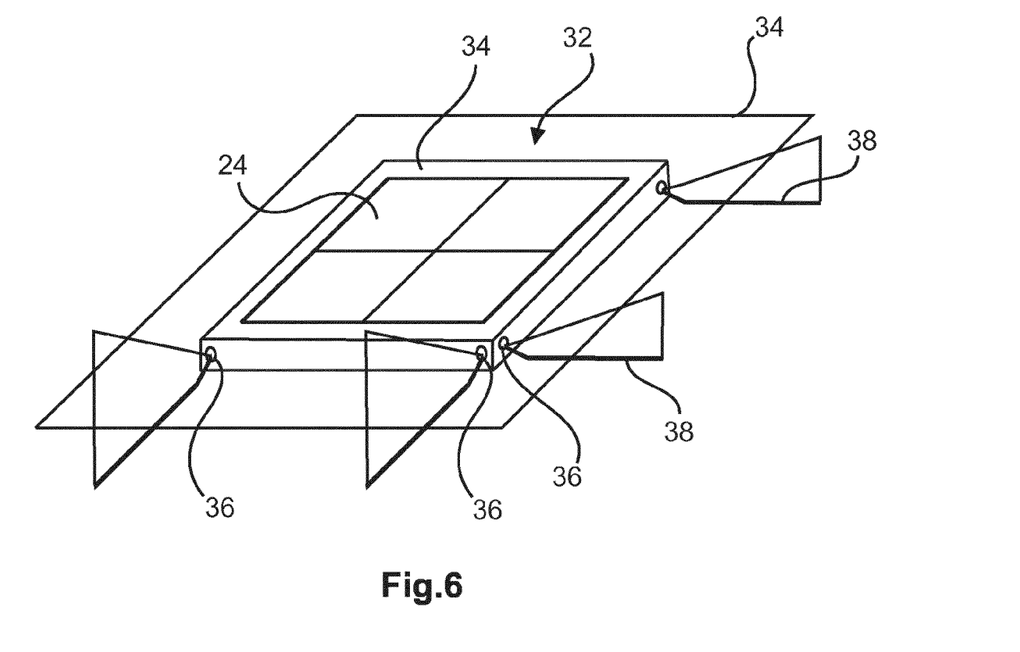
FIG. 6 schematically shows an example of a detector receiving device and a detector with a support surface of the detector attachment.

In FIG. 6, a detector attachment 34 is shown, where the detector attachment 34 is a detector receiving device. In other words, the detector 24 can be handled separately and also be exchanged, if necessary. The detector attachment 34 also comprises multiple second light projection devices 36 which generate fan shaped light resulting in a line shaped second light patterns 38.

The term "receiving" can mean that the detector is enclosed at the edges by a frame-like arrangement, which comprises the light projection devices 36. It can also be an arrangement of separate parts which are connected to the detector 24.

For example, a detector receiving device can also be a parallel plane, on which the detector 24 is mounted. Also different imaging methods may be used which require different detector panels. For example, detectors of different size can be used depending on the imaged region.

In another example, detectors can be mounted to the detector receiving device by sliding in, clicking in, screws or other means. In another example, the detector receiving device or detector attachment 34 can also be separate parts, for instance rigid wires extending from the edges or corners from a detector 24. The projection surface 32 is in the shown example a support surface for the detector attachment 34. This support surface for the detector attachment 34 can be, for instance, a separate plastic layer, which is inserted between a mattress and the detector attachment 34. An advantage would be that a good reflection and projection behavior can be achieved, if no suitable projection surface 32 is available.

Figure 7:
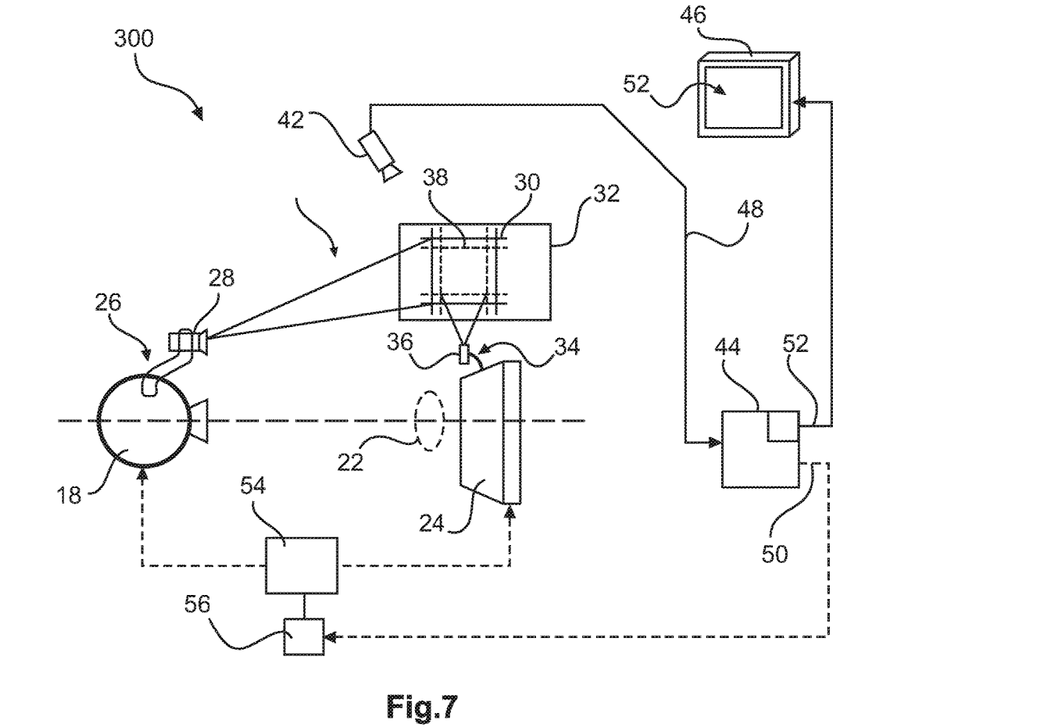
FIG. 7 schematically illustrates a medical X-ray imaging system with an automated adjustment of the spatial arrangement of X-ray tube and detector.

In FIG. 7, an extended medical X-ray imaging system 300 is shown, which comprises an X-ray tube 18 and a detector 24, which are configured and arranged to acquire image information of a region of interest 22. Analog to FIG. 2, a tube attachment 26 with a first light projection device 28 and a detector attachment 34 with a second light projection device 36 is shown. The first light projection device 28 generates a first light pattern 30 and the second light projection device 36 generates a second light pattern 38, wherein both light patterns 30, 38 are projected onto a projection surface 32. The example in FIG. 7 further comprises additional supplementary components which help to simplify and at least partly automate the alignment process of the X-ray tube 18 and the detector 24 relative to each other. For this purpose, the extended medical X-ray imaging system 300 further comprises a capturing device 42, a processor 44 and a display device 46.

The capturing device 42 is adapted to acquire image information 48 of the first and second light patterns 30, 38 and to provide this image information 48 to the processor 44. The processor 44 is adapted to detect a deviation from the determined alignment of the first light pattern 30 with the second light pattern 38 based on the acquired image information 48. The processor 44 is further adapted to generate modification data 50 based on the determined deviation, wherein the modification data 50 indicates changes in the spatial arrangement of the X-ray tube 18 and the detector 24 relative to each other, which would at least partly compensate the deviation. The processor 44, furthermore, generates or translates the modification data 50 to modification instructions 52, which are provided to the display device 46. The modification instructions 52 can be displayed on the display device 46, for example, as arrow symbols or other suitable instruction techniques. The display device 46 can be arranged such that a user can easily view the displayed information on the display device 46 during the alignment process. Modification instructions can be any representations of modification data, which are understood by human users. For example, an arrow on a screen indicates a direction, in which an X-ray tube 18 has to be moved or turned to achieve an alignment between the X-ray tube 18 and the detector 24.

"Modification data" are information, which indicate how the spatial arrangement between the X-ray tube 18 and the detector 24 has to be changed to achieve an alignment between the projected light patterns 30, 38. A determination of the deviation can take place, for example, by image processing by the processor 44 and detection of known patterns and detection of parallel/non-parallel lines, symmetry detection or similar.

A "compensation of the deviation" can mean that the degree of misalignment between the tube 18 and the detector 24 is decreased.

"Acquire image information of the first and second patterns" relates to capturing an image of the projection area on the projection surface 32, where the alignment of the first and second pattern 30, 38 takes place.

A display device 46 can be, for instance, an LCD or TFT screen.

A capturing device 42 may be a camera device, which is directed to the projection surface 32 where the light patterns 30, 32 are projected. The camera may be, for instance, a typical camera with a CCD chip for visual light or, in another example, the capturing device 42 is able to capture infrared and/or ultraviolet light in case infrared or ultraviolet is issued by the light projection devices 28, 36.

An advantage of this additional functionality can be that the workflow and image quality is improved. Furthermore, scattered X-ray dose to the radiologist can be limited, because the alignment and X-ray image capturing can be done from a location outside the patient room.

In a further example, the medical X-ray imaging system 300 further comprises an actuator 54 with an actuator control unit 56. The control unit 56 of the actuator is configured to control the actuator 54 to automatically modify the spatial arrangement of the X-ray tube 18 and the detector 24 relative to each other based on the modification data 50. In other words, the processor 44 generates and provides the information for the necessary spatial arrangement adjustment of X-ray tube 18 and detector 24 and provides this modification data 50 to the actuator control unit 56. The actuator control unit 56 then translates this modification data 50 into control signals, which are provided to the actuator 54, which then performs the spatial position adjustments of the X-ray tube 18 and/or the detector 24.

An advantage, which can be realized is that by the full or partly automation of the adjustment process, the workflow can be further simplified and shortened.

Figure 8:
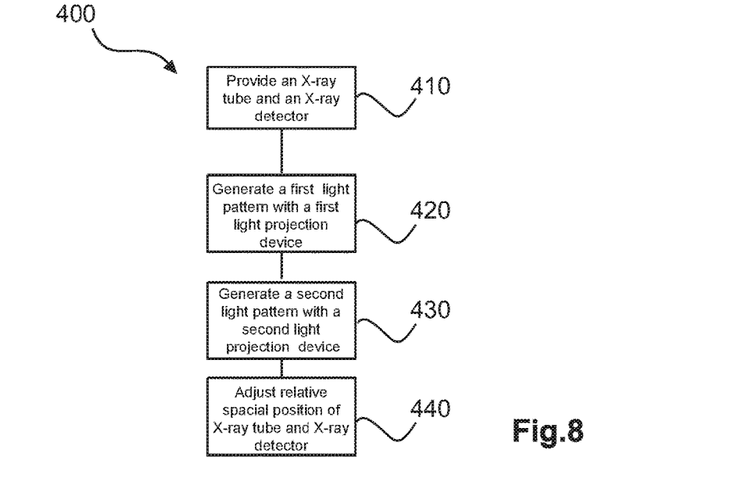
FIG. 8 schematically illustrates an example of a method for aligning an X-ray tube relative to a detector.

In FIG. 8, an example of a method 400 for aligning an X-ray tube relative to a detector is shown. The method 400 comprises a step 410 of providing an X-ray tube and an X-ray detector. In a following step 420, a first light pattern is generated with a first light projection device, wherein the first light projection device is adapted to generate a first visible light pattern on a projection surface. In next step 430, a second light pattern is generated with a second light projection device, wherein the second light projection device is adapted to generate a second visible light pattern on the projection surface. The first light pattern on the projection surface is in a determined spatial alignment with the second light pattern on the projection surface in the event that the X-ray tube and the detector are in a correctly spatially arranged relative to each other.

In step 440, a spatial position of the X-ray tube and the detector relative to each other is adjusted such that the first light pattern is in the determined spatial alignment with the second light pattern.

The determined spatial alignment of the first and second light beam can comprise at least a partial superposition of visible light patterns generated by the first and second light beam on a projection plane.

In another example a method for automatic spatial arrangement adjustment of an x-ray tube and a detector is provided, wherein the method comprises the steps of providing a capturing device, a processor, an actuator control unit and an actuator. In a next step the capturing device acquires image information of a projection surface, wherein the projection surface comprises a first light pattern and a second light pattern. In a next step the processor determines a deviation from a predetermined alignment of the two light patterns relative to each other. In a next step the processor provides modification information to an actuator control unit. In a last step the actuator control unit controls actuators to change a spatial position of the x-ray tube and/or the detector such that the two light patterns come into alignment.

It has to be noted that embodiments of the invention are described with reference to different embodiments. However, a person skilled in the art will gather from the above and the following description that, unless otherwise notified, any combination between features relating to different embodiments is considered to be disclosed within this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An alignment arrangement for X-ray imaging, comprising
   a tube attachment with a first light projection device;
   a detector attachment with a second light projection device;
   wherein the tube attachment is configured to mount the first light projection device to an X-ray tube;
   wherein the detector attachment is configured to connect the second light projection device to an X-ray detector;
   wherein the first light projection device is adapted to generate a first light pattern on a projection surface;
   wherein the second light projection device is adapted to generate a second light pattern on the projection surface;
   wherein the first light pattern is in a predetermined spatial relation with the second light pattern on the projection surface in the event that the tube attachment and detector attachment are correctly spatially arranged relative to each other.

2. The alignment arrangement according to claim 1, wherein the first and/or second light pattern(s) on the projection surface comprise a plurality of lines.

3. The alignment arrangement according to claim 1, wherein the light pattern of the second light projection device indicates a spatial position of edges of the detector attachment.

4. The alignment arrangement according to claim 1, wherein, when the predetermined spatial relation of the first and second light patterns exists, both patterns at least partially superpose on the projection surface.

5. The alignment arrangement according to claim 1, wherein the second light projection device of the detector attachment generates fan shaped light approximately perpendicular to the projection surface.

6. The alignment arrangement according to claim 1, wherein the first and second light patterns have different light colors.

7. The alignment arrangement according to claim 1, wherein the first and/or second light projection device(s) is/are configured to adapt the light pattern to a plurality of predetermined spatial arrangements of the tube attachment and the detector attachment.

8. The alignment arrangement according to claim 1, wherein the detector attachment is a detector receiving device configured to support and/or accommodate a detector.

9. A medical X-ray imaging system, comprising:
   an X-ray tube;
   a detector; and
   an alignment arrangement according to claim 1;
   wherein the X-ray tube and the detector are adapted to acquire an image of a region of interest of an object;
   wherein a spatial arrangement of the X-ray tube and the X-ray detector relative to each other is adjustable;
   wherein the tube attachment is mounted to the X-ray tube and the detector attachment is mounted to the detector such that the X-ray tube and the detector are in a correct spatial arrangement relative to each other when the first light pattern is in the predetermined spatial relation with the second light pattern on the projection surface.

10. The medical X-ray imaging system according to claim 9, wherein the projection surface is at least partly a support surface of an object and/or a support surface for the detector attachment.

11. The medical X-ray imaging system according to claim 9, wherein the light pattern of the second light projection device indicates spatial positions of edges of the detector.

12. The medical X-ray imaging system according to claim 9, further comprising
   a capturing device;
   a processor;
   a display device;
   wherein the capturing device is adapted to acquire image information of the first and second light patterns and to provide the image information to the processor;
   wherein the processor is adapted to determine a deviation from the predetermined spatial relation of the first light pattern with the second light pattern based on the image information;
   wherein the processor is adapted to generate modification data based on the determined deviation, wherein the modification data indicates changes that need to be made in the spatial arrangement of the X-ray tube and the detector relative to each other, in order to at least partly compensate for the deviation; and
   i) wherein an actuator with an actuator control unit is provided, and wherein the control unit of the actuator is configured to control the actuator to automatically modify the spatial arrangement of the X-ray tube and the detector relative to each other based on the modification data;
   and/or
   ii) wherein the display device is configured to provide modification instructions to a user based on the modification data.

13. A method for aligning an X-ray tube relative to a detector, the method comprising the steps of:
   providing an X-ray tube and an X-ray detector;
   generating a first visible light pattern on a projection surface with a first light projection device mounted to the X-ray tube by means of a tube attachment;
   generating a second visible light pattern on the projection surface with a second light projection device connected to the X-ray detector by means of a detector attachment,
   wherein the first light pattern on the projection surface has a determined spatial alignment with the second light pattern on the projection surface in the event that the X-ray tube and the detector are correctly spatially arranged relative to each other; and
   adjusting spatial position of the X-ray tube and the detector, relative to each other, such that the first light pattern is brought into the determined spatial alignment with the second light pattern.

* * * * *